(12) United States Patent
Sharpe, Jr. et al.

(10) Patent No.: US 9,255,578 B2
(45) Date of Patent: Feb. 9, 2016

(54) SYSTEMS AND METHODS TO MONITOR PUMP CAVITATION

(75) Inventors: Joseph H. Sharpe, Jr., Glen Allen, VA (US); Gary Hawkins, Clarendon Hills, IL (US); Robert Skeirik, Knoxville, TN (US)

(73) Assignee: FISHER-ROSEMOUNT SYSTEMS, INC., Round Rock, TX (US)

( * ) Notice: Subject to any disclaimer, the term of this patent is extended or adjusted under 35 U.S.C. 154(b) by 615 days.

(21) Appl. No.: 13/563,294

(22) Filed: Jul. 31, 2012

(65) Prior Publication Data

US 2014/0039805 A1 Feb. 6, 2014

(51) Int. Cl.
| | |
|---|---|
| G01N 11/00 | (2006.01) |
| F04D 15/00 | (2006.01) |
| F04B 49/06 | (2006.01) |
| F04D 15/02 | (2006.01) |
| F04B 11/00 | (2006.01) |
| G01N 29/14 | (2006.01) |

(52) U.S. Cl.
CPC ............ *F04D 15/0088* (2013.01); *F04B 11/00* (2013.01); *F04B 49/065* (2013.01); *F04D 15/0245* (2013.01); *G01N 29/14* (2013.01)

(58) Field of Classification Search
USPC .......................................................... 702/24
See application file for complete search history.

(56) References Cited

U.S. PATENT DOCUMENTS

| | | | |
|---|---|---|---|
| 4,060,716 A | 11/1977 | Pekrul et al. | |
| 5,332,356 A | 7/1994 | Gulich | |
| 5,772,403 A * | 6/1998 | Allison et al. | 417/44.2 |
| 6,056,008 A * | 5/2000 | Adams et al. | 137/487.5 |
| 6,206,646 B1 | 3/2001 | Bucher | |
| 6,655,922 B1 | 12/2003 | Flek | |
| 6,663,349 B1 | 12/2003 | Discenzo et al. | |
| 6,839,660 B2 | 1/2005 | Eryurek et al. | |
| 6,882,960 B2 | 4/2005 | Miller | |
| 6,954,713 B2 | 10/2005 | Eryurek | |
| 7,142,990 B2 | 11/2006 | Bouse et al. | |
| 7,290,450 B2 | 11/2007 | Brown et al. | |
| 7,623,986 B2 | 11/2009 | Miller | |
| 2004/0093174 A1 * | 5/2004 | Lander | 702/56 |
| 2008/0215255 A1 * | 9/2008 | Stockner et al. | 702/34 |
| 2012/0042732 A1 | 2/2012 | Zhu et al. | |
| 2012/0055149 A1 | 3/2012 | Vonderwell | |

FOREIGN PATENT DOCUMENTS

| | | |
|---|---|---|
| EP | 1298511 A1 | 4/2003 |
| JP | H01273898 A | 11/1989 |

OTHER PUBLICATIONS

Intellectual Property Office of Great Britain, "Search Report", issued in connection with British patent application No. 1312997.8, dated on Jul. 9, 2014, 6 pages.

* cited by examiner

*Primary Examiner* — Paul D Lee
(74) *Attorney, Agent, or Firm* — Hanley, Flight and Zimmerman, LLC (57) ABSTRACT

Systems and methods to monitor pump cavitation are disclosed. An example method includes monitoring a pressure parameter and a vibration parameter associated with an asset in an operating process unit. The example method includes calculating a manipulated pressure value based on the pressure parameter. The example method includes calculating a manipulated vibration value based on the vibration parameter. The example method includes determining a state of cavitation associated with the asset based on at least one of the manipulated pressure value or the manipulated vibration value.

20 Claims, 8 Drawing Sheets

SYSTEMS AND METHODS TO MONITOR PUMP CAVITATION

FIELD OF THE DISCLOSURE

This disclosure relates generally to process control systems and/or asset management systems and, more particularly, to systems and methods to monitor pump cavitation.

BACKGROUND

Operating process units and/or systems, like those used in the oil and gas production industry, refining, petrochemical and other manufacturing facilities, typically include significant equipment assets, such as pumps, heat exchangers, cooling towers, etc. The condition, health, integrity, and/or performance of such assets are essential to the efficiency and/or safety of processing plants.

SUMMARY

Systems and methods to monitor pump cavitation are disclosed. An example method includes monitoring a pressure parameter and a vibration parameter associated with an asset in an operating process unit. The example method includes calculating a manipulated pressure value based on the pressure parameter. The example method includes calculating a manipulated vibration value based on the vibration parameter. The example method includes determining a state of cavitation associated with the asset based on at least one of the manipulated pressure value or the manipulated vibration value.

An example system includes a monitoring application to monitor a pressure parameter and a vibration parameter associated with an asset in an operating process unit. The example system includes a pressure analyzer to calculate a manipulated pressure value based on the pressure parameter. The example system includes a vibration analyzer to calculate a manipulated vibration value based on the vibration parameter. The example system includes a cavitation analyzer to determine a state of cavitation associated with the asset based on at least one of the manipulated pressure value or the manipulated vibration value.

An example tangible computer-readable storage medium includes instructions that, when executed, cause a computing device to monitor a pressure parameter and a vibration parameter associated with an asset in an operating process unit. The example instructions cause the computing device to calculate a manipulated pressure value based on the pressure parameter. The example instructions cause the computing device to calculate a manipulated vibration value based on the vibration parameter. The example instructions cause the computing device to determine a state of cavitation associated with the asset based on at least one of the manipulated pressure value or the manipulated vibration value.

DETAILED DESCRIPTION

Industry averages suggest that roughly five percent of production capacity is lost each year due to unplanned downtime. One of the most significant causes for such downtime is equipment failure, which can often exceed forty percent of unplanned downtime. Not only can an unexpected failure lead to lost production and increased maintenance costs, in some circumstances, an equipment failure may result in fires, environmental release of noxious materials, and/or other unsafe circumstances. While known process control systems may monitor the most critical equipment by wiring sensors that communicate with a host system, it is often cost prohibitive to monitor all assets online and/or in real-time. Accordingly, the remaining equipment is manually checked through clipboard workarounds and periodic handheld measurement and monitoring devices to obtain isolated data concerning the condition, health, integrity and/or performance of the equipment or asset. The result of this known approach is that many assets (e.g., pumps) within an operating process unit and/or system are running without being monitored most of the time, thereby increasing the risk of failures, leaks, fires, and/or other undesirable impacts on the performance and/or safety of the entire system.

Cavitation is one of the leading causes of pump failure. Cavitation occurs in a pump (e.g., a centrifugal pump) when there is insufficient pressure within the pump casing to maintain a fluid in a liquid state. When the fluid within the pump is unable to maintain a liquid state, vapor pockets and/or small bodies of gas contained in the liquid (e.g., bubbles) form within the pump. Cavitation may be caused by a restriction in a suction line of the pump, a low level in an upstream component or vessel, high flow causing high piping pressure drop, high fluid temperature, changing fluid composition, continued operation below a particular (e.g., minimum) flow, etc. Vapor pockets or bubbles associated with cavitation may eventually cause damage to components of the pump. For example, cavitation may erode material from the impeller, wear down the pump housing and/or seal, and/or cause pumps seals to leak. Such damage to components of the pump may result in a failure of the pump. Early detection of pump cavitation (e.g., before the pump fails due to cavitation) may reduce maintenance cost and/or process impact.

Avoiding equipment damage, environmental incidents, and/or negative impacts on business as described above depends on being able to detect changes in process variables and/or equipment conditions as they occur (i.e., in substantially real-time via online monitoring). Furthermore, being able to relate multiple measurements provides greater predictive value in assessing the likelihood of the onset of asset failures (e.g., due to pump cavitation) as it provides a more complete picture of the condition of the asset. Thus, even where individual measurements on a particular piece of equipment are collected, the engineer collecting the measurements is unlikely to appreciate the significance of the individual measurements in light of other parameters associated with the asset. For example, a pump may be periodically inspected to measure whether it is operating within acceptable vibrational limits. However, when such a measurement is made in the field, there is no way of correlating this with other measurements, such as flow rate, pressure, and/or other parameters that are being monitored in connection with the process control system. Without having all this information available and properly understood, these individual measurements will have less value in determining the present health of the asset and/or less ability in anticipating impending failures than when multiple measurements are integrated into a comprehensive view of the overall condition of the asset.

Such a technique, as is disclosed herein, is made possible by recognizing that, while there are many potential causes of equipment failures, it is possible to generalize a method that combines specific equipment health measurements with process measurements to make a more sophisticated analysis of what might be occurring than what is known in the art. Using this integrated analysis, the system and methods described herein enable the determination of an overall asset health status or value and the identification of the most critical parameters affecting the condition of an asset to an operator, engineer, maintenance staff, and/or other plant personnel (hereinafter collectively referred to as an operator). Specifically, using this integrated analysis, the systems and methods described herein enable the determination of a cavitation (or pre-cavitation) state of a pump and the identification of the most critical parameters affecting the condition of the pump (e.g., pressure and/or vibration) to an operator. Furthermore, the teachings of this disclosure involve systems and methods that provide an earlier detection of potential asset failures (e.g., pump cavitation) than is known in the art by the integration of measurements that are sensitive to most of the major failure modes, including both equipment and process data (e.g., pressure and/or vibration data), analysis of the combined information to produce an overall indication of the likelihood of a near term failure, and presentation to operators in a manner that permits them to quickly understand the state of the asset and the possible failure.

Figure 1:
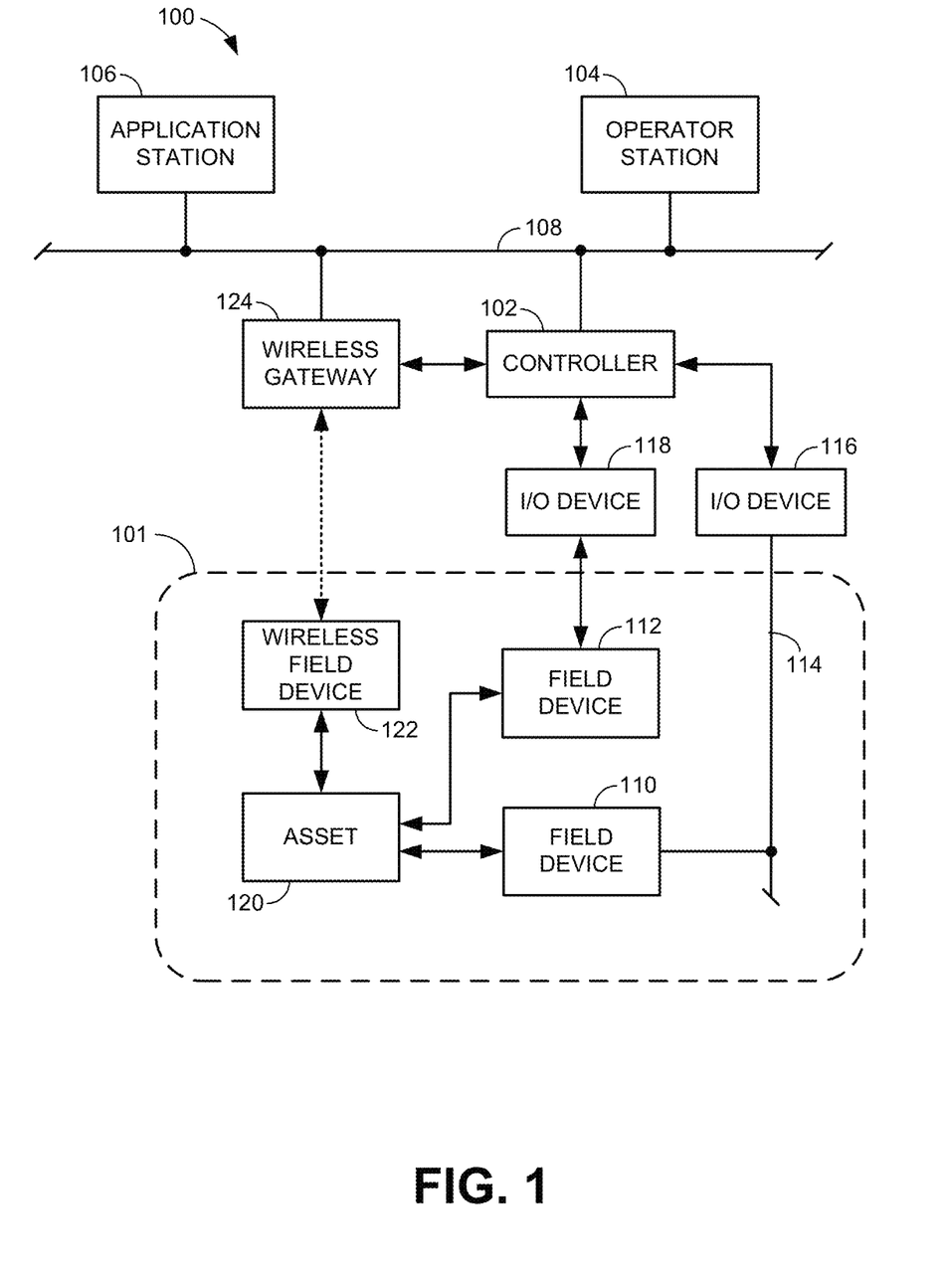
FIG. 1 is a schematic illustration of an example operating process unit in an example process control system within which the teachings of this disclosure may be implemented.

FIG. 1 is a schematic illustration of an example process control system 100 implementing an operating process unit 101 in accordance with the teachings of this disclosure. The example system 100 may be a distributed control system (DCS), a supervisory control and data acquisition (SCADA) system and/or any other type of process system that monitors and/or controls the example operating process unit 101. Additionally or alternatively, the example operating process unit 101 may be monitored and/or associated with an asset management system (AMS) regardless of whether the system 100 is providing any control of the operating process unit 100. As illustrated in FIG. 1, the example system 100 includes one or more process controllers (one of which is designated at reference numeral 102), one or more operator stations (one of which is designated at reference numeral 104), and one or more application stations (one of which is designated at reference numeral 106). The example process controller 102, the example operator station 104, and/or the example application station 106 are communicatively coupled via a bus and/or local area network (LAN) 108, which is commonly referred to as an area control network (ACN).

The example operator station 104 of FIG. 1 allows an operator to review and/or operate one or more operator display screens and/or applications that enable the operator to view process control system variables, states, conditions, alarms; change process control system settings (e.g., set points, operating states, clear alarms, silence alarms, etc.); configure and/or calibrate devices within the operating process unit 101; perform diagnostics of devices within the operating process unit 101; and/or otherwise manage and interact with devices within the operating process unit 101.

The example application station 106 of FIG. 1 may be configured to perform one or more information technology applications, user-interactive applications and/or communication applications. For example, the application station 106 may be configured to perform primarily process control-related applications, while another application station (not shown) may be configured to perform primarily communication applications that enable the operating process unit 101 to communicate with other devices or systems using any desired communication media (e.g., wireless, hardwired, etc.) and protocols (e.g., HTTP, SOAP, etc.). In some examples, a remote session may be established on the example application station 106 to view and/or interact with the applications on the example operator station 104. Additionally, the example application station 106 and/or the example operator station 104 may include and/or implement an asset monitoring application (e.g., the example asset monitoring application of FIG. 3) that may be part of an asset management software (AMS) application. The asset monitoring application is associated with a user interface (e.g., the example user interface of FIG. 3) to display information and/or provide visual indications of the condition, health, integrity, and/or performance of assets within the operating process unit 101. An example manner of implementing the example application station 106 of FIG. 1 is described below in connection with FIG. 3.

The example operator station 104 and the example application station 106 of FIG. 1 may be implemented using one or more workstations and/or any other suitable computer systems and/or processing systems. For example, the operator station 104 and/or application station 106 could be implemented using single processor personal computers, single or multi-processor workstations, etc. Furthermore, the example operator station 104 and/or the application station 106 may connect to another network from which other users (e.g., maintenance and/or equipment engineers), via separate workstations, may have access. Additionally or alternatively, the example operating process unit 101 may contain other workstations within the same network (e.g., a maintenance station and/or an engineering station) to provide separate functionality associated with the operating process unit 101.

The example LAN 108 of FIG. 1 may be implemented using any desired communication medium and protocol. For example, the example LAN 108 may be based on a hardwired and/or wireless Ethernet communication scheme. However, any other suitable communication medium(s) and/or protocol(s) could be used. Further, although a single LAN 108 is illustrated in FIG. 1, more than one LAN and/or other alternative pieces of communication hardware may be used to provide redundant communication paths between the example systems of FIG. 1.

The example controller 102 of FIG. 1 is coupled to a plurality of smart field devices 110, 112 via a data bus 114 and input/output (I/O) devices 116, 118, such as an I/O card communicatively coupled to the controller 102. In the illustrated example, the field device 110 includes a pressure sensor and the field device 112 includes a vibration sensor. The smart field devices 110, 112 may be and/or include any other devices such as valves, actuators, sensors, etc. The smart field devices 110, 112 of the illustrated example are HART compliant devices that communicate via the data bus 114 using the well-known HART communication protocol. However, the smart field devices 110, 112 may be any Fieldbus and/or Profibus compliant devices, in which case the smart field devices 110, 112 communicate via the data bus 114 using the well-known Foundation Fieldbus and/or Profibus communication protocols. Additional I/O devices (similar and/or identical to the I/O devices 116, 118) may be coupled to the controller 102 to enable additional groups of smart field devices, which may be Foundation Fieldbus devices, HART devices, etc., to communicate with the controller 102.

As shown in the illustrated example, a smart field device 122 may be a wireless device that relays data to a wireless gateway 124. In some such examples, the wireless gateway 124 interfaces with the controller 102 (e.g., via a wireless I/O card). Using such wireless technology enables the reduction in cost and complexity of wiring and configuring hardwired cables for each device. Additionally or alternatively, in some examples, the wireless gateway 124 connects directly to the ACN (e.g., the LAN 108) to enable transmitted data to be read directly by the application station 106 using Object Linking and Embedding (OLE) for Process Control (OPC). Accordingly, while the teachings of this disclosure may be implemented in connection with a process control system (e.g., via the example controller 102), the teachings of this disclosure may also be implemented completely independent of a process control system. In some examples, the field devices 110, 112 may be wireless devices.

In addition to the example smart field devices 110, 112, one or more non-smart field devices may be communicatively coupled to the example controller 102. A non-smart field device may be, for example, conventional 4-20 milliamp (mA) or 0-24 volts direct current (VDC) devices that communicate with the controller 102 via respective hardwired links connected to corresponding I/O cards associated with the controller 102. In the illustrated example of FIG. 1, the smart field devices 110, 112, 122 are associated with an asset (e.g., a pump 120) to measure and/or control parameters associated with the pump 120 in the operating process unit 101. The asset of the illustrated example is the pump 120. However the asset may be any asset within an operating process unit such as a heat exchanger, an air cooled exchanger, a furnace, a fired heater, a blower, a fin fan, a cooling tower, a distillation column, a compressor, a pipe, a valve, a vessel, a well head, a tank, a centrifuge, etc. In some examples, the field devices 110, 112, 122 may be directly integrated with the pump 120 and/or other assets. In other examples, the field devices 110, 112, 122 may be separate devices that may be in communication with, or otherwise interact with, the pump 120 and/or other assets. Furthermore, others of the field devices 110, 112, 122 in the illustrated examples may be configured to monitor and/or control other components within the operating process unit 101.

The example controller 102 of FIG. 1 may be, for example, a DeltaV™ controller sold by Fisher-Rosemount Systems, Inc., an Emerson Process Management company. However, any other controller could be used instead. Further, while only one controller 102 is shown in FIG. 1, additional controllers and/or process control platforms of any desired type and/or combination of types could be coupled to the LAN 108. In any case, the example controller 102 performs one or more process control routines associated with the system 100 that have been generated by a system engineer and/or other system operator using the operator station 104 and/or the example application station 106 and which have been downloaded to and/or instantiated in the controller 102.

The field device 110 includes a pressure sensor to measure pressure within a discharge line of the pump 120. The field device 112 includes a vibration sensor to measure vibration at the pump 120. An example of the pump 120 and field device 110, 112 configuration is illustrated below in connection with FIG. 2. The pressure and/or vibration measurements collected by the field devices 110, 112 are passed to the application station 106 via the I/O devices 116, 118 and the controller 102. The application station 106 uses the pressure and/or vibration measurements to detect a pre-cavitation and/or cavitation state of the pump 120. This pre-cavitation and/or cavitation state of the pump 120 is relayed to an operator via, for example, a display, to enable the operator to remedy an issue within the pump 120 resulting in cavitation. For example, the measurements may be used to detect a pre-cavitation state (e.g., the measurements reflect an impending cavitation state) and the operator may be informed of the pre-cavitation state. If cavitation then occurs, the operator may be informed of the advancement of the pre-cavitation state to one of cavitation. Early detection of cavitation using the field devices 110, 112 enables the operator to remedy issues within the pump 120 without and/or before pump failure, thereby reducing likelihood of production losses and minimizing maintenance costs.

While FIG. 1 illustrates an example system 100 within which the methods and apparatus to assess the condition, health, integrity, and/or performance of an asset (e.g., the pump 120) and/or to the likelihood of the onset of potential asset failures (e.g., due to pump cavitation) described in greater detail below may be advantageously employed, the methods and apparatus to control information presented to operators and/or engineers described herein may, if desired, be advantageously employed in other process plants and/or process control systems of greater or less complexity (e.g., having more than one controller, across more than one geographic location, etc.) than the illustrated example of FIG. 1.

Figure 2:
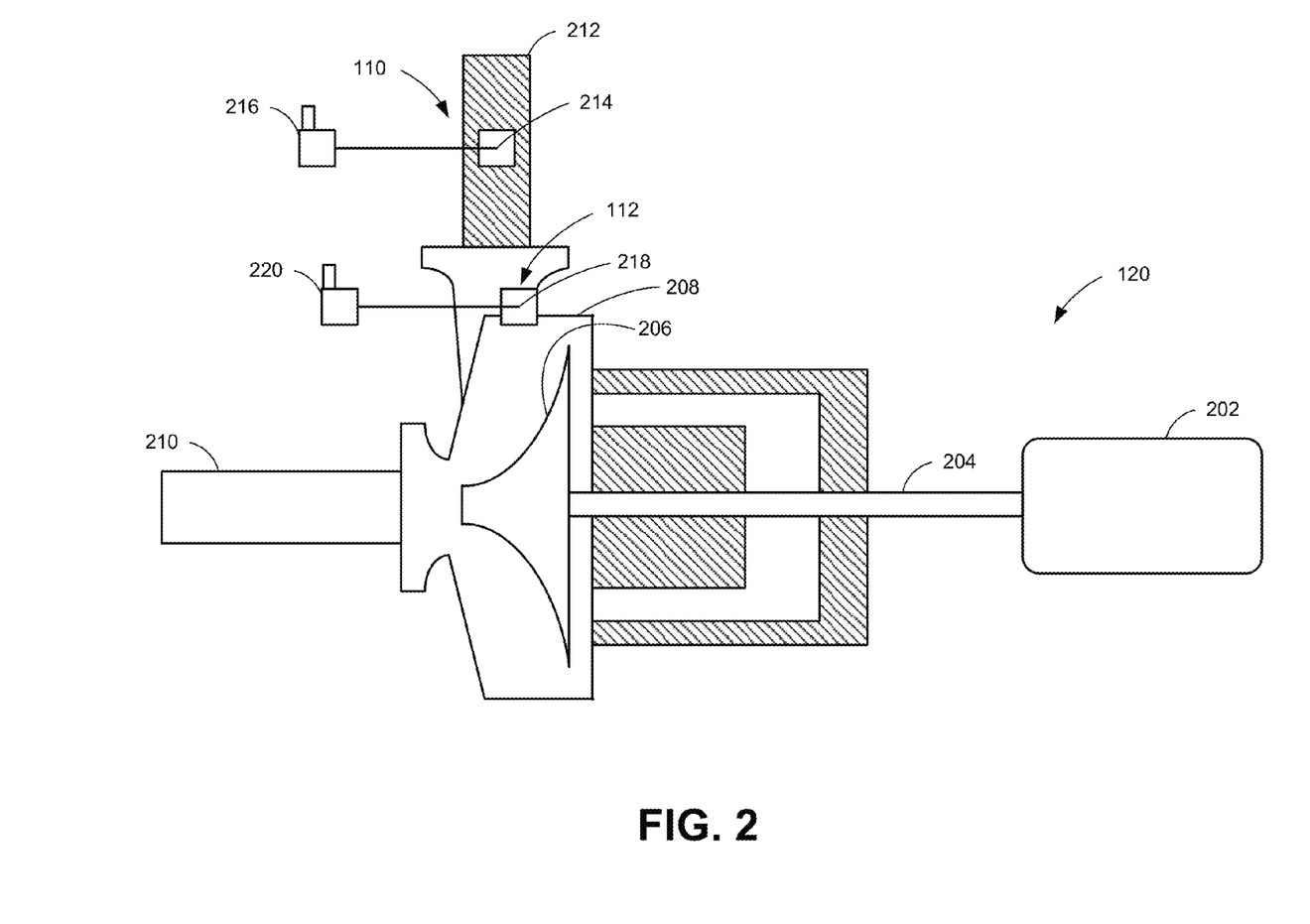
FIG. 2 illustrates an example manner of implementing the example pump and field devices of FIG. 1.

FIG. 2 illustrates an example manner of implementing the example pump 120 and the example field devices 110, 112 of FIG. 1. In the example of FIG. 2, the pump 120 includes a motor 202, a shaft 204, an impeller 206, a pump casing 208, a suction line 210, and a discharge line 212. The motor 202 rotates the shaft 204, which rotates the impeller 206. The impeller 206 draws a liquid through the suction line 210 and forces the liquid out through the discharge line 212.

In the illustrated example, the field device 110 includes a pressure sensor 214 located on the discharge line 212 and a pressure transmitter 216. The pressure sensor 214 measures the pressure within the discharge line 212 and the pressure transmitter 216 transmits the pressure measurements to the I/O device 116 of FIG. 1. The pressure sensor 214 may measure the pressure within the discharge line 212 continuously, periodically, and/or aperiodically. The period for measurement by the pressure sensor 214 may be set automatically (e.g., to a default setting) or may be set and/or selected by an operator. The pressure transmitter 216 may transmit the pressure measurements to the I/O device 116 continuously, periodically, and/or aperiodically. The period for transmitting the pressure measurements may be set automatically (e.g., to a default setting) or may be set and/or selected by an operator. The pressure transmitter 216 may communicate with the I/O device 116 via a wired and/or wireless connection.

In the illustrated example, the field device 112 includes a vibration sensor 218 located on the pump casing 208 and a vibration transmitter 220. The vibration sensor 218 measures vibration and/or impact on the pump 120. For example, the vibration sensor 218 may measure vibration associated with rotation of the shaft 204. The vibration sensor 218 measures the vibration and/or impact at the pump casing 208 and the vibration transmitter 220 transmits the vibration measurements to the I/O device 118. The vibration sensor 218 may measure the vibration at the pump casing 208 continuously, periodically, and/or aperiodically. The period for measurement by the vibration sensor 218 may be set automatically (e.g., to a default setting) or may be set and/or selected by an operator. The vibration transmitter 220 may transmit the vibration measurements to the I/O device 118 continuously, periodically, and/or aperiodically. The period for transmitting the vibration measurements may be set automatically (e.g., to a default setting) or may be set and/or selected by an operator. The vibration transmitter 220 may communicate with the I/O device 118 via a wired and/or wireless connection.

The pressure and/or vibration measurements are sent to the application station 106 of FIG. 1 via the I/O gateways 116, 118 and the controller 102 for use in detecting pre-cavitation and/or cavitation of the pump 120. Pump cavitation may be detected from an increase (e.g., a significant increase) in pressure variation measured by the pressure sensor 214 and/or combined with an increase in the vibration measured by the vibration sensor 218.

While the example field device 110 of FIG. 2 includes the pressure sensor 214 and the pressure transmitter 216, any other number and/or combination of sensors, transmitters, and/or other devices may be used to implement the field device 110. While the example field device 112 of FIG. 2 includes the vibration sensor 218 and the vibration transmitter 220, any other number and/or combination of sensors, transmitters, and/or other devices may be used to implement the field device 112. Furthermore, the field devices 110, 112 may be located on and/or within any other component of the pump 120 to collect pressure and/or vibration measurements.

While the example field devices 110, 112 of FIG. 2 communicate with the example controller 102 via I/O gateway devices 116, 118, the devices 110, 112 may communicate with other controllers and/or I/O devices not shown in FIGS. 1 and/or 2. The example application station 106 may communicate with the devices using standard communication protocols such as OPC, MODBUS or Open Database Connectivity ("ODBC").

Figure 3:
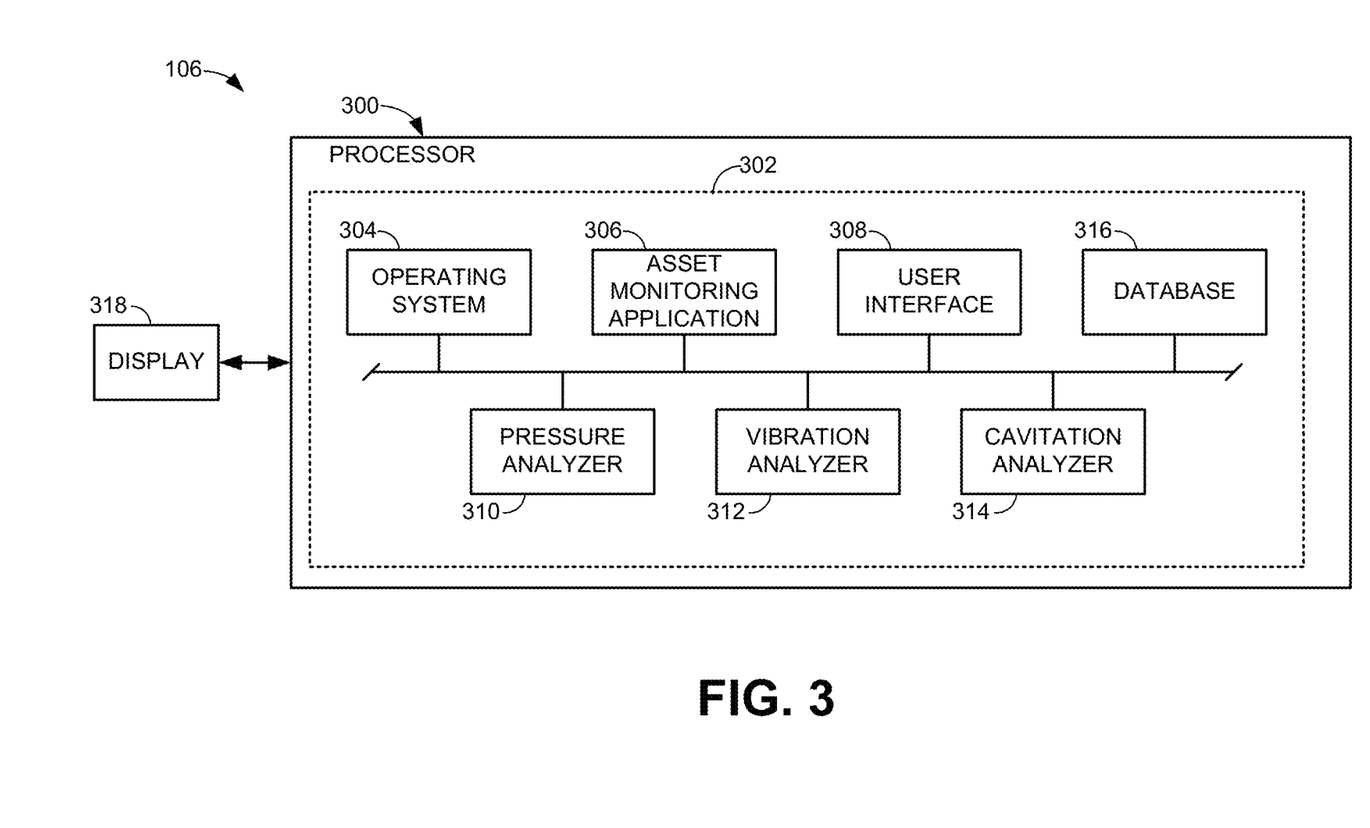
FIG. 3 illustrates an example manner of implementing the example operator station of FIG. 1.

FIG. 3 illustrates an example manner of implementing the example application station 106 of FIG. 1. While the following description is provided with respect to the application station 106, the example manner of implementing the example application station 106 may also be used to implement the example operator station 104 of FIG. 1. The example application station 106 of FIG. 3 includes at least one programmable processor 300. The example processor 300 of FIG. 3 executes coded instructions present in a main memory 302 of the processor 300 (e.g., within a random-access memory (RAM) and/or a read-only memory (ROM)). The processor 300 may be any type of processing unit, such as a processor core, a processor and/or a microcontroller. The processor 300 may execute, among other things, an example operating system 304, an example asset monitoring application 306, an example user interface 308, an example pressure analyzer 310, an example vibration analyzer 312, an example cavitation analyzer 314, and an example database 316. An example operating system 304 is an operating system from Microsoft®. The example main memory 302 of FIG. 3 may be implemented by and/or within the processor 300 and/or may be one or more memories and/or memory devices operatively coupled to the processor 300.

Figure 4:
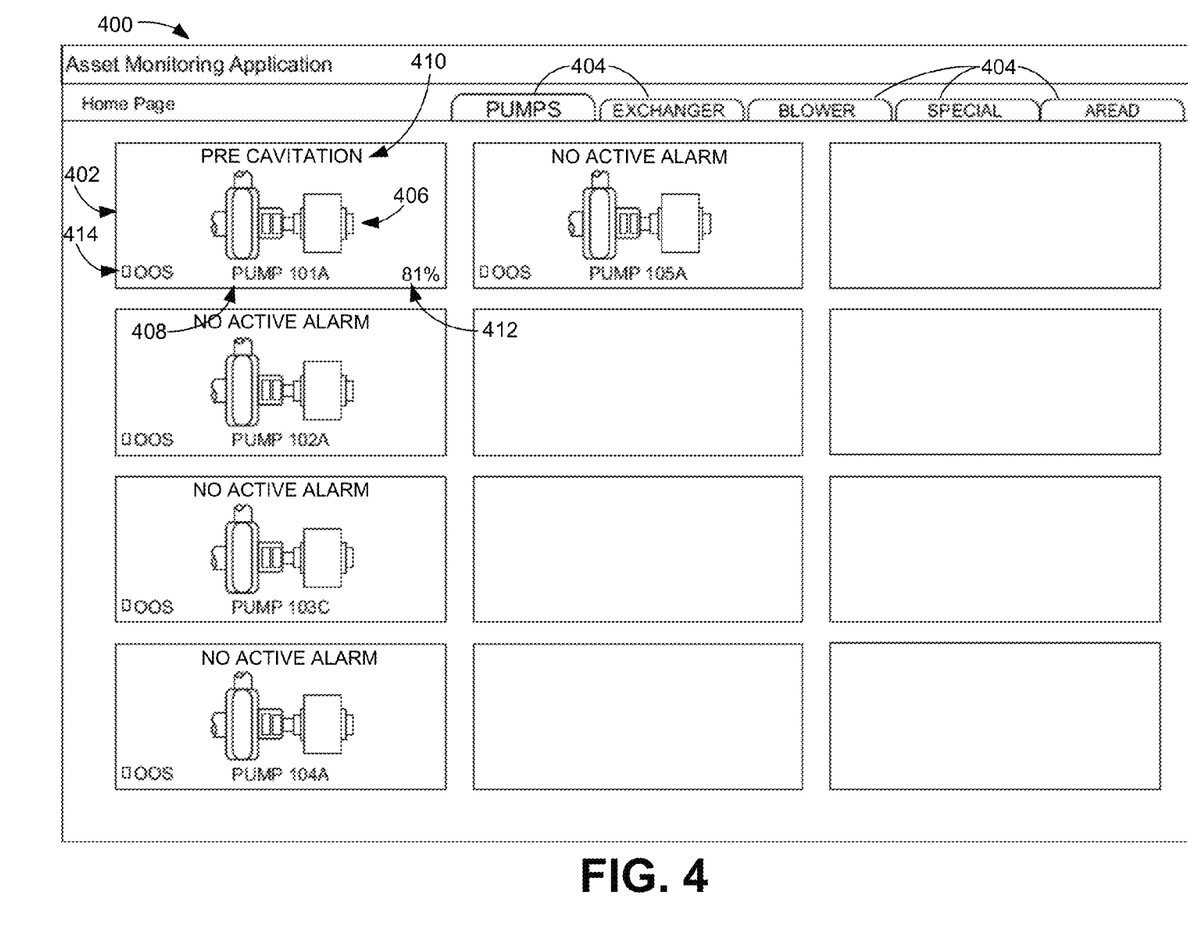
FIG. 4 illustrates an example home page associated with the user interface of FIG. 3.
Figure 5:
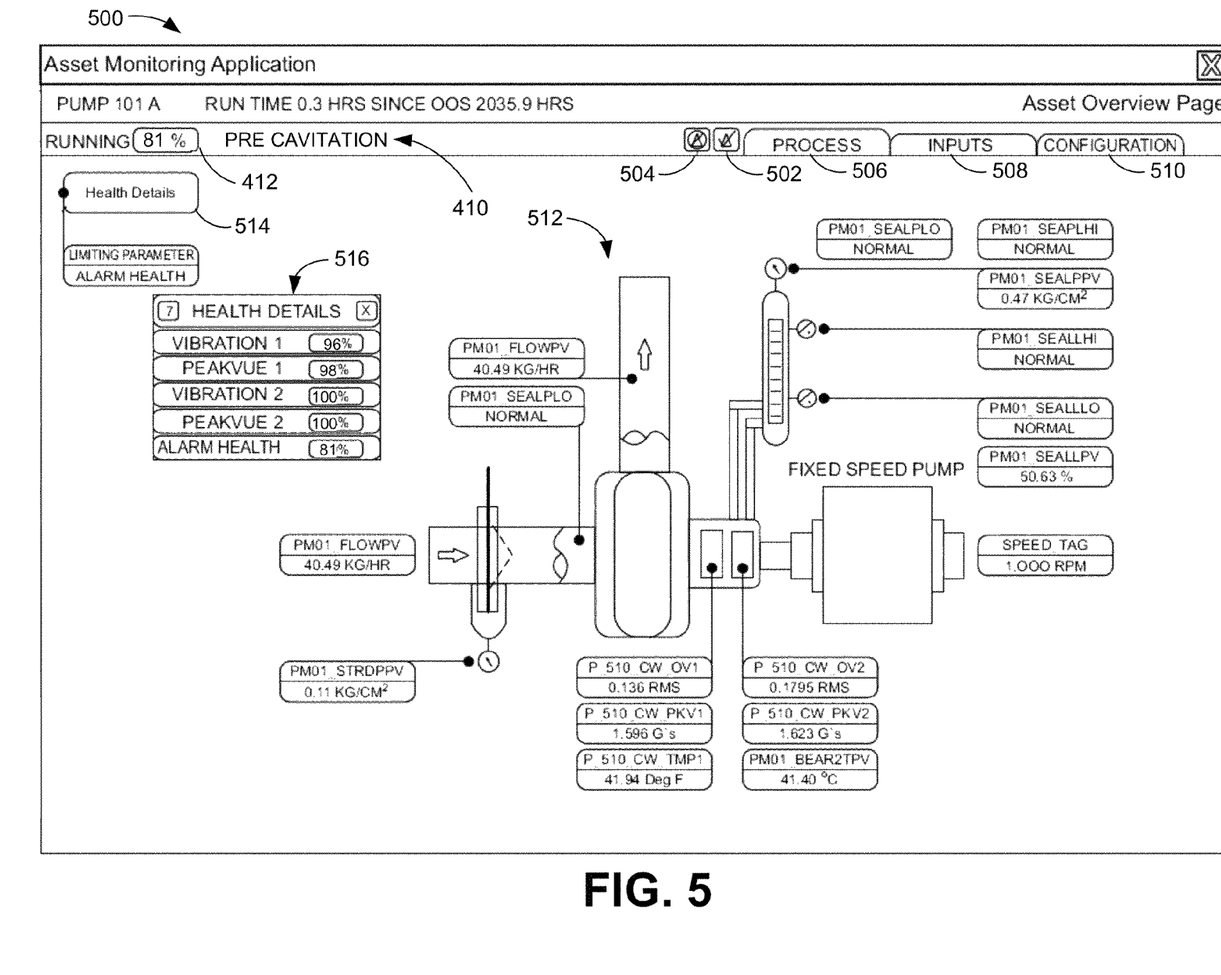
FIG. 5 illustrates an example process tab of an example asset overview page of FIG. 4 associated with the user interface of FIG. 3.
Figure 6:
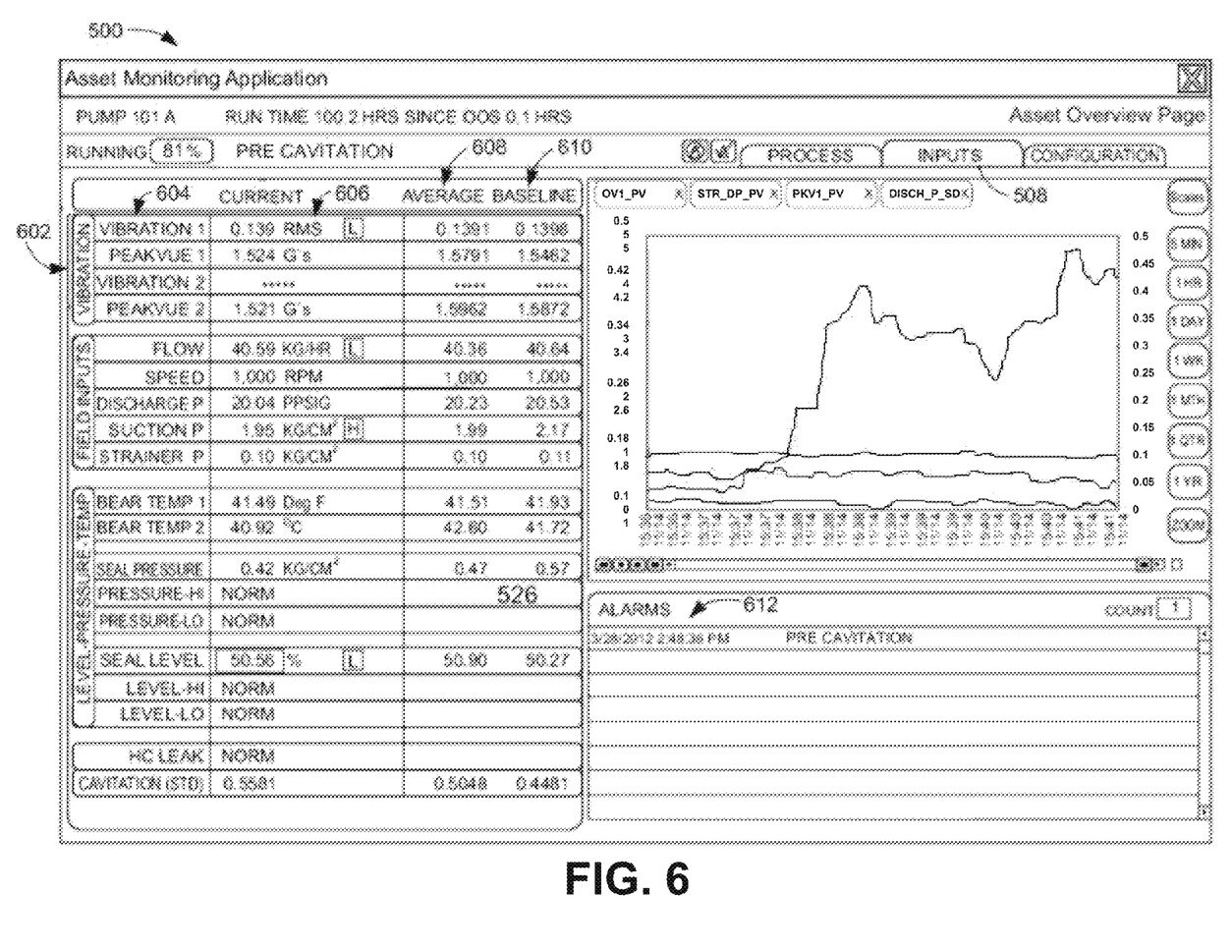
FIG. 6 illustrates an example input tab of the example asset overview page of FIG. 4 associated with the user interface of FIG. 3.

To allow operators to interact with the example processor 300, the example application station 106 of FIG. 3 includes any type of display 318. Example displays 318 include, but are not limited to, a computer monitor, a computer screen, a television, a mobile device (e.g., a smart phone, a Blackberry™ and/or an iPhone™), etc., capable of displaying user interfaces and/or applications implemented by the processor 300 and/or, more generally, the example application station 106. The example operating system 304 of FIG. 3 displays and/or facilitates the display of the example user interface 308 associated with the example asset monitoring application 306 by and/or at the example display 318. Example displays associated with the user interface 308 and/or asset monitoring application 306 are illustrated in FIGS. 4-6.

The example asset monitoring application 306 receives data via one or more of the field devices 110, 112 of FIG. 1 measuring parameters associated with the operating process unit 101 and/or, more particularly, parameters associated with the operation and/or integrity of assets within the operating process unit 101 (e.g., the example pump 120 of FIG. 1). Parameters associated with the operation and/or control of an operating process unit are herein referred to as process parameters. Examples of process parameters include measurements corresponding to parameters such as temperature, pressure, flow rate, etc. In the illustrated example, the field device 110 collects a process parameter, specifically the pressure within a discharge line of the pump 120. Parameters associated with the condition, state, health, integrity, and/or performance of a piece of equipment (e.g., asset) are herein referred to as equipment parameters. For example, for rotary assets (e.g., pumps, fans, blowers, compressors, etc.), equipment parameters may correspond to a speed of rotation, a vibration, a temperature of bearings, an oil level, a seal leak, etc. In the illustrated example, the field device 112 collects an equipment parameter, specifically the vibration at a pump casing of the pump 120. In some examples, measured parameters may be relevant to both the condition and/or integrity of an asset as well as the operation and/or control of a process within which the asset is running.

In the illustrated example, the example pressure analyzer 310 analyzes pressure measurements received via the asset monitoring application 306. In some examples, the example pressure analyzer 310 analyzes other data received via the asset monitoring application 306 that is associated with other process parameters. For example, a low voltage parameter and/or a "Bad Value" parameter received via the transmitter 218 may be used to signal whether the pressure input is valid. The pressure analyzer 310 manipulates the received pressure measurements to be used by the cavitation analyzer 314 (e.g., calculates statistical parameters) to detect pre-cavitation and/or cavitation states of the pump 120. In some examples, the pressure analyzer 310 calculates the standard deviation of a particular number of pressure measurements. For example, the pressure analyzer 310 may calculate the standard deviation of the last five consecutive pressure measurements. The particular number of pressure measurements used in the standard deviation calculation may be automatic (e.g., a default setting) and/or may be set by an operator. In some examples, the pressure analyzer 310 calculates an average standard deviation of a particular number of standard deviation values. For example, the pressure analyzer 310 calculates the average standard deviation of the last fifteen standard deviation values. The particular number of standard deviation values used in the average standard deviation calculation may be automatic (e.g., a default setting) and/or may be set by the operator. In some examples, the pressure measurements are manipulated (e.g., the averages and/or standard deviations are calculated) at the field device 110 (e.g., at the transmitter 216 of FIG. 2). The pressure analyzer 310 may manipulate the pressure measurements in a variety of ways (e.g., various statistical calculations may be used) to increase the likelihood of detecting pre-cavitation and/or cavitation states of the pump 120.

The pressure measurements collected at the pump 120 are expected to vary during operation of the pump 120. Thus, the actual value of a pressure measurement is less helpful in detecting a pre-cavitation or cavitation state of the pump 120. Accordingly, the pressure analyzer 310 calculates standard deviation values of the pressure measurements to detect changes in pressure at the pump 120 indicative of a pre-cavitation or cavitation state. The manipulated pressure measurements (e.g., the average and/or standard deviations) are used at the cavitation analyzer 314 to determine if the pump 120 is operating in a pre-cavitation and/or cavitation state. Analyzing the standard deviations of the pressure measurements compensates for variations in pump operating conditions and, thus, the cavitation analyzer 314 is less likely to falsely detect a pre-cavitation and/or cavitation state.

In the illustrated example, the vibration analyzer 312 analyzes vibration and/or impact measurements received via the asset monitoring application 306. In some examples, the example vibration analyzer 312 analyzes other data received via the asset monitoring application 306 that is associated with other equipment parameters. The vibration analyzer 312 manipulates the received vibration measurements to be used by the cavitation analyzer 314 to detect pre-cavitation and/or cavitation states of the pump 120.

In some examples, the vibration analyzer 312 calculates an overall vibration associated with the pump 120. Overall vibration may be primarily sinusoidal in nature and may include measurements at a low frequency. In some examples, the vibration analyzer 312 may filter out rotational energy from the overall vibration measurements by filtering out low frequencies to analyze impact on the pump 120. Impact on the pump 120 may be indicative of a fault associated with the pump 120. For example, the pump 120 may develop a bearing defect or a gear defect, may have insufficient lubrication, may be in a pre-cavitation or cavitation state, etc. In some examples, the vibration analyzer 312 analyzes peak vibration measurements (e.g., vibration measurements in a high frequency range) to analyze impact on the pump 120. Vibration measurements may refer to overall vibration, peak vibration or impact, etc.

In some examples, the vibration analyzer 312 calculates an average vibration for a particular number of vibration measurements. For example, the vibration analyzer 312 may calculate the average of the last ten vibration measurement values. The particular number of vibration measurements used in the averaging calculation may be automatic (e.g., a default setting) and/or may be set by an operator. In some examples, the vibration analyzer 312 calculates standard deviations and/or ranges of the vibration measurements. The particular number of vibration measurements used in the standard deviation and/or range calculations may be automatic (e.g., a default setting) and/or may be set by the operator. In some examples, the vibration measurements are manipulated (e.g., the averages and/or standard deviations are calculated) at the field device 112 (e.g., at the transmitter 220 of FIG. 2). The vibration analyzer 312 may manipulate the vibration measurements in a variety of ways (e.g., various statistical calculations may be used) to increase the likelihood of detecting pre-cavitation and/or cavitation states of the pump 120. The manipulated vibration measurements (e.g., the average vibration measurements) may be used at the cavitation analyzer 314 to determine if the pump 120 is operating in a pre-cavitation and/or cavitation state.

In the illustrated example, the cavitation analyzer 314 compares the manipulated pressure (e.g. standard deviation) and/or manipulated vibration measurements (e.g. average vibration) relative to reference values or baselines for the parameters. In some examples, the baseline for the pressure measurements is defined by an operator. In some examples, the cavitation analyzer 314 captures the pressure baseline from measured values of the pressure during operating conditions of the pump 120 where an operator is confident that pump 120 is operating correctly (e.g., during normal operating conditions). In some examples, the pressure baseline is captured soon after the pump 120 is configured and first put into operation to reduce the impact of wear and/or degradation in conditions of the pump 120 after extended use. The pressure baseline in some examples is a standard deviation of expected pressure measurements, an average of expected pressure measurements, and/or an average standard deviation of expected pressure measurements. In some such examples, the pressure baseline may be further adjusted by a multiplying factor configured by an operator based on the particular needs and/or operation of the process control system.

In some examples, the pump 120 may have a range of conditions and/or operational states within which it functions. Accordingly, in some such examples, different pressure baselines may be captured or otherwise defined to be applied for each respective operational state of the pump 120. In some examples, pressure measurements may vary depending on some other variable state parameter. Thus, in some such examples where the pressure measurements are dependent on a variable state parameter, a characteristic curve or signature is captured to serve as a dynamic pressure baseline of normal operating conditions as a function of the variable state parameter.

In some examples, the baseline for the vibration measurements is defined by an operator. In some examples, the baseline for the vibration measurements is a value of "0." In some examples, the cavitation analyzer 314 captures the vibration baseline from measured values of the vibration during operating conditions of the pump 120 where an operator is confident that pump 120 is operating correctly (e.g., during normal operating conditions). In some examples, the vibration baseline is captured soon after the pump 120 is configured and first put into operation to reduce the impact of wear and/or degradation in conditions of the pump 120 after extended use. The vibration baseline in some examples is a standard deviation and/or range of expected vibration measurements, an average of expected vibration measurements, and/or an average standard deviation and/or range of expected vibration measurements. In some such examples, the vibration baseline may be further adjusted by a multiplying factor configured by an operator based on the particular needs and/or operation of the process control system.

In some examples, the pump 120 may have a range of conditions and/or operational states within which it functions. Accordingly, in some such examples, different vibration baselines may be captured or otherwise defined to be applied for each respective operational state of the pump 120. In some examples, vibration measurements may vary depending on some other variable state parameter. For example, vibrations of the pump 120 may vary as a function of the speed at which the pump 120 is running. Thus, the vibration baseline may vary along an entire range of speed within which the pump 120 operates. Accordingly, in some examples, where the vibration is dependent on a variable state parameter, a characteristic curve or signature is captured to serve as a dynamic vibration baseline of normal operating conditions as a function of the variable state parameter.

The example database 316 of FIG. 3 stores data received via the example asset monitoring application 306 and/or via an operator, which may include pressure and/or vibration baselines. Additionally, the database 316 may store any of the data output via any of the example pressure analyzer 310, the example vibration analyzer 312, or the example cavitation analyzer 314.

From the manipulated pressure and/or vibration measurements and the pressure and/or vibration baselines, the cavitation analyzer 314 detects a pre-cavitation and/or cavitation state of the pump 120. The pre-cavitation and/or cavitation state indicates the severity of deviation of the manipulated pressure and/or vibration at the pump 120 from expected values (e.g., the manipulated pressure and/or vibration baselines). The detection of a pre-cavitation and/or cavitation state activates alarms to be presented to an operator via the display 318. Alarms may be configured with differing severity. For example, some alarms may be primarily for informational purposes, while others give warnings, and yet others indicate that which is critical. Thus, in some examples, a warning may be provided to the operator when the pump 120 is in a pre-cavitation state and the warning may be increased to a more significant alarm when the pump 120 reaches a cavitation state.

To detect a pre-cavitation state of the pump 120, the cavitation analyzer 314 compares the manipulated pressure measurement from the pressure analyzer 310 to a pressure baseline. For example, the manipulated pressure measurement (e.g., the average standard deviation) is compared to a factor multiplied by the pressure baseline. As described above, the factor and/or the pressure baseline may be set automatically (e.g., at default settings) and/or may be set by an operator. If the manipulated pressure measurement exceeds the multiplied pressure baseline for a particular number of cycles, the cavitation analyzer 314 determines the pump 120 is in a pre-cavitation state and will set a pre-cavitation alarm. The number of cycles may be an amount of time, a number of collected measurements, etc. and may be set automatically (e.g., at a default setting) and/or may be set by an operator. In some examples, if the manipulated pressure measurement exceeds the pressure baseline by a particular amount and/or exceeds a different pressure baseline by a particular amount, the cavitation analyzer 314 determines that the pump 120 is in a cavitation state and will set a cavitation alarm.

In some examples, the cavitation analyzer 314 determines if the manipulated vibration measurement from the vibration analyzer 312 exceeds a vibration baseline by a particular amount. If the manipulated vibration measurement exceeds the vibration baseline by the particular amount, the cavitation analyzer 314 may set a high vibration or vibration increase detected alarm. In some examples, once the pre-cavitation alarm has been triggered based on pressure, the cavitation analyzer 314 determines if the manipulated vibration measurement from the vibration analyzer 312 exceeds a vibration baseline by a particular amount. If the manipulated vibration measurement exceeds the vibration baseline by the particular amount, the cavitation analyzer 314 increases the pre-cavitation alarm (e.g., sets a higher warning level) and/or sets a cavitation alarm. In such an example, an operator may desire to know when the vibration of the pump 120 reaches a certain threshold when the discharge pressure of the pump 120 is above its corresponding pressure baseline (e.g., alarm limit). In some examples, an operator may desire to know when the operating conditions of the pump 120 reach a certain threshold prior to cavitation (e.g., a pre-cavitation) and, more critically, when the pump 120 is cavitating. Integrating the analysis of process parameters (e.g., pressure) and equipment parameters (e.g., vibration) in this manner enables operators to predict the likely onset of potential failures (e.g., due to cavitation) earlier on than with known methods, thereby reducing the cost due to downtime and/or maintenance.

While an example manner of implementing the example application station 106 of FIG. 1 has been illustrated in FIG. 3, the data structures, elements, processes and devices illustrated in FIG. 3 may be combined, divided, re-arranged, omitted, eliminated and/or implemented in any other way. Further, the example operating system 304, the example asset monitoring application 306, the example user interface 308, the example pressure analyzer 310, the example vibration analyzer 312, the example cavitation analyzer 314, the example database 316, and/or, more generally, the example application station 106 of FIG. 3 may be implemented by hardware, software, firmware and/or any combination of hardware, software and/or firmware. Further still, the example application station 106 may include additional elements, processes and/or devices instead of, or in addition to, those illustrated in FIG. 3, and/or may include more than one of any or all of the illustrated data structures, elements, processes and/or devices.

FIGS. 4-6 illustrate example displays associated with the user interface 308 and/or the asset monitoring application 306 of FIG. 3. The example displays of FIG. 4 present parameters, measurements, and/or alarms related to an asset (e.g., a pump) to facilitate operator action to remedy any issues reflected in the parameters, measurements, and/or alarms. FIG. 4 illustrates an example overview page or home page 400 that may be displayed via the display 318 of FIG. 3. In the illustrated example, the home page 400 provides an asset summary graphic 402 for each asset (e.g., the pump 120) in the operating process unit. In some examples, assets in the asset summary graphic 402 may be grouped by process plant, by process area within a particular process plant, and/or by asset type. For example, as shown in FIG. 4, a selected tab 404 corresponds to pumps (asset type) and shows five asset summary graphics 402 corresponding to five separate pumps.

Each asset summary graphic 402 provides general information regarding the condition, health, and/or performance of the corresponding asset. Specifically, each asset summary graphic 402 may provide an asset image 406 providing a visual representation of the type of asset (e.g., pump). Each asset summary graphic 402 may also include a process tag 408 identifying the particular asset associated with its corresponding graphic 402 to which a particular asset summary graphic corresponds (e.g., PUMP 101A). Additionally, in some examples, the asset summary graphic 402 provides a limiting alarm label 410 that identifies an active alarm (e.g., the most severe or critical alarm) associated with the asset. In the illustrated example, PUMP 101A is in a pre-cavitation state and, thus, the alarm label 410 reads "PRE CAVITATION." If an asset has reached a cavitation state, the alarm label 410 may read "CAVITATION." In some examples, each asset summary graphic 402 provides an indication of the overall health and/or state of the asset by showing an asset health value 412 corresponding to the asset. The asset health value 412 may be a numerical indication of a lowest equipment health value or process health value determined for the asset. The asset health value 412 is represented as a percentage with 100% corresponding to the best health. In the illustrated example, the asset health value 412 for PUMP 101A is 81%. The asset health value 412 for PUMP 101A may decrease if and/or when the asset reaches a cavitation state. The asset summary graphic 402 may include an out of service (OOS) checkbox 414. If selected, a command issues to bring the asset out of service or back into service depending on its current state. When an asset is taken out of service, all alarms (e.g., the pre-cavitation alarm) become inactive.

FIGS. 5-6 illustrate an example asset overview page 500 of the user interface 308 of FIG. 3 having multiple sub-views or tabs. Each asset within an operating process unit has a corresponding asset overview page 400 that may be accessed by selecting the corresponding asset summary graphic 402 on the home page 400 of FIG. 4. The asset overview page 500 may include basic information associated with the asset such as a process tag, a run time indicating the time since the asset last started running, a total running time since the asset was brought into service, an operating status (e.g., Running/Stopped, Active/Inactive, etc.), etc. In the illustrated example, the overview page 500 includes an alarm acknowledgement button or icon 502 and a silence horn alarm button or icon 504. The overview page 500 also includes the asset health value 412 (e.g., 81%) and the limiting alarm label 410 (e.g., PRE CAVITATION) described above in connection with FIG. 4.

The example asset overview page 500 may have separate sub-views or tabs including a process tab 506 (as shown and described in FIG. 4), an inputs tab 508 (as shown and described in FIG. 6), and a configuration tab 510 that enable an operator to view, access, and/or interact with data related to various aspects of the associated asset. The content of the process tab 506 illustrated in FIG. 5 provides a process graphic 512 that shows the asset in connection with the relevant components of the process system. In the illustrated example, the content of the process tab 506 may include a health detail button or icon 514. By selecting the health detail button 514, a separate window or pop-up 516 may appear providing the current equipment health value for each configured equipment and/or process parameter. For example, the parameters listed in the pop-up may contribute to the overall asset health value 412 and may be used to determine a pre-cavitation and/or cavitation alarm (e.g., indicated in the alarm label 410).

FIG. 6 illustrates the example input tab 508 of the example asset overview page 500 of FIG. 5 associated with the user interface 308 of FIG. 3. As illustrated in FIG. 6, within the inputs tab 508 an input table 602 is provided with a parameter column 604, a current column 606, an average column 608, and a baseline column 610. The parameter column 604 lists each parameter associated with the asset. In some examples the parameters may be grouped by type. The current column 606 provides the current value and corresponding units associated with each parameter of the parameter column 604. The average column 608 provides average values for the corresponding monitored parameters based on a running average. The baseline column 610 provides the configured baseline data associated with each of the parameters. The baseline data serves as a reference from which limits may be calculated and equipment health values may be determined. The parameters, averages, and/or baselines are used to determine if the asset is in a pre-cavitation and/or cavitation state. As shown in the illustrated example of FIG. 6, the inputs tab 508 may also include an alarms window 612. The alarms window 612 may provide a list of all alarms along with their activation and deactivation times. Once an alarm condition returns to normal, the corresponding alarm may be removed from the alarms window 612. In the illustrated example, the asset is in a pre-cavitation state and the "PRE CAVITATION" alarm is provided in the alarms window 612. The example displays of FIGS. 4-6 present parameters, measurements, and/or alarms related to the asset to facilitate operator action to remedy any issues reflected in the parameters, measurements, and/or alarms.

Figure 7:
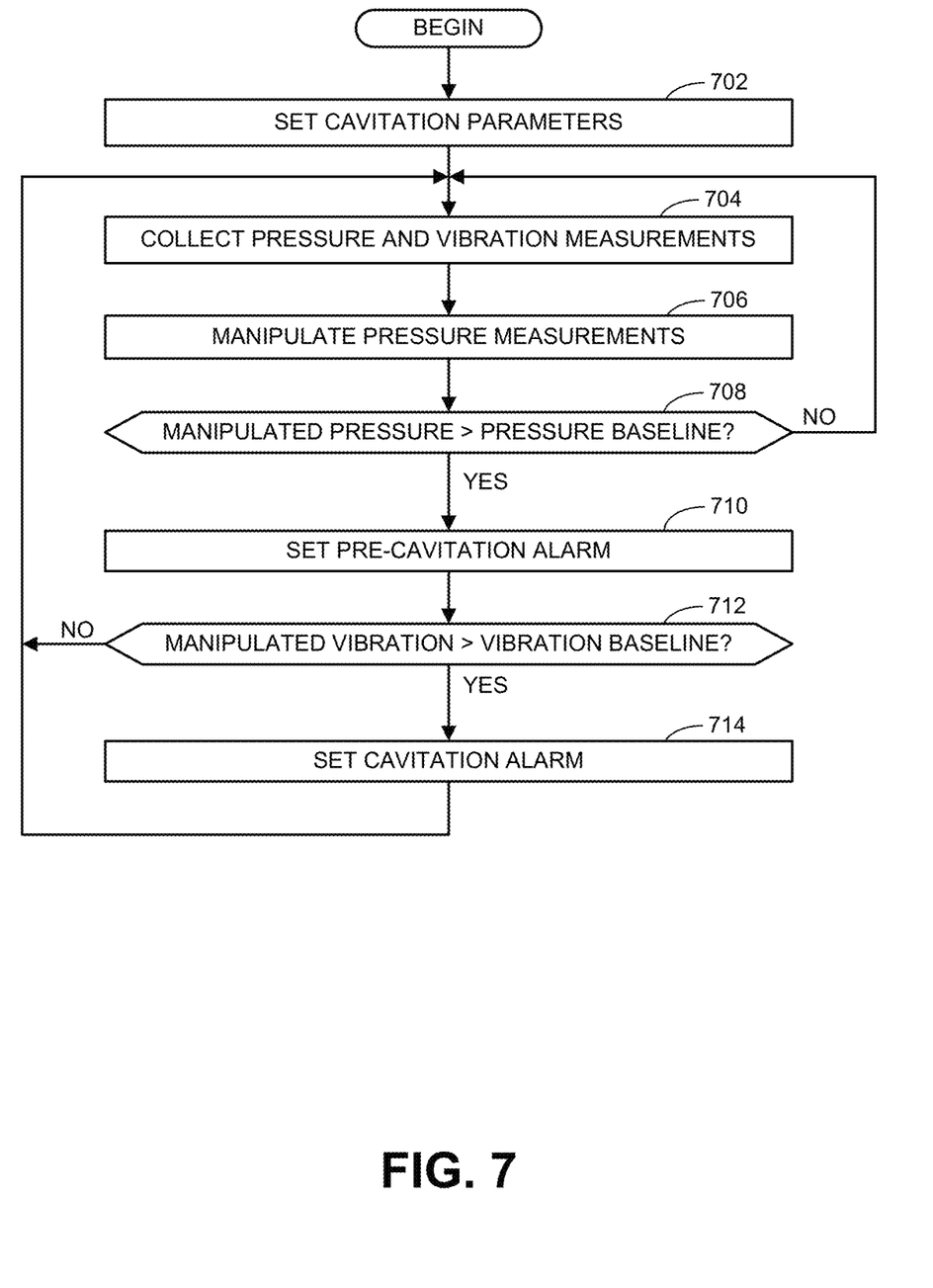
FIG. 7 is a flowchart representative of an example process that may be carried out to implement the example operator station of FIGS. 1 and/or 3.

FIG. 7 is a flowchart representative of an example process that may be carried out to implement the example application station 106 of FIGS. 1 and/or 3. More particularly, the example process of FIG. 7 may be representative of machine readable instructions that comprise a program for execution by a processor such as the processor 812 shown in the example computer 800 discussed below in connection with FIG. 8. The program may be embodied in software stored on a tangible computer readable medium such as a CD-ROM, a floppy disk, a hard drive, a digital versatile disk (DVD), a BluRay disk, or a memory associated with the processor 812. Alternatively, some or all of the example process of FIG. 7 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, one or more of the example operations of FIG. 7 may be implemented manually or as any combination(s) of any of the foregoing techniques, for example, any combination of firmware, software, discrete logic and/or hardware. Further, although the example process is described with reference to the flowchart illustrated in FIG. 7, many other methods of implementing the example application station 106 of FIGS. 1 and/or 3 may alternatively be used. For example, the order of execution of the blocks may be changed, and/or some of the blocks described may be changed, eliminated, or combined. Additionally, any or all of the example process of FIG. 7 may be performed sequentially and/or in parallel by, for example, separate processing threads, processors, devices, discrete logic, circuits, etc.

As mentioned above, the example process of FIG. 7 may be implemented using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example process of FIG. 7 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

The example process of FIG. 7 begins by setting cavitation parameters at the cavitation analyzer 314 (block 702). Cavitation parameters refer broadly to measurement settings, manipulation settings, baseline settings, alarm settings, etc. Measurement settings include, for example, the frequency that parameters are measured (e.g., how often pressure and/or vibration measurements are collected), the frequency that collected measurements are to be received (e.g., how often measurements are sent from the field devices 110, 112 of FIG. 1 to the application station 106), etc. Manipulation settings include, for example, how a standard deviation of pressure and/or vibration measurements is calculated (e.g., how many measurements are included in the standard deviation calculation), how pressure and/or vibration measurements are averaged (e.g., the number of measurements that are averaged), how standard deviations are averaged (e.g., how many standard deviations are included in the averaging calculation), etc. Baseline settings include, for example, pressure and/or vibration baseline values, pressure and/or vibration multiplying factors (e.g., a factor to be multiplied by a baseline value), length of an execution cycle (e.g., a length of time that a pressure and/or vibration measurement exceeds a baseline to trigger an alarm), etc. Alarm settings include, for example, checking a vibration measurement when a pre-cavitation alarm has been set, etc. The cavitation parameters may be set automatically (e.g., to default values), may be collected (e.g., collecting baseline data to set a baseline), and/or may be set by an operator via the user interface 308 of FIG. 3. The cavitation parameters may be stored in the database 316.

The example process of FIG. 7 collects pressure and/or vibration measurements associated with the pump 120 of FIG. 1 (block 704). The application station 106 of FIGS. 1 and/or 3 collect pressure and/or vibration measurements from the field devices 110, 112 of FIG. 1. The asset monitoring application 306 passes the pressure and/or vibration measurements to the pressure analyzer 310 and/or the vibration analyzer 312 for analysis.

The example process of FIG. 7 manipulates the pressure measurements at the pressure analyzer 310 (block 706). In some examples, the pressure analyzer 310 calculates a standard deviation for a particular number of pressure measurements. In some examples, the pressure analyzer 310 calculates an average standard deviation using a particular number of standard deviation values. The pressure analyzer 310 manipulates the pressure measurements according to the manipulation parameters set at block 702.

The example process of FIG. 7 determines if the manipulated pressure exceeds a pressure baseline at the cavitation analyzer 314 (block 708). The pressure baseline is used in the comparison according to the baseline parameters set at block 702. For example, the cavitation analyzer 314 determines if the average standard deviation of the pressure measurements exceeds a particular factor multiplied by a pressure baseline for a particular number of execution cycles. If the cavitation analyzer 314 determines that the manipulated pressure does not exceed the pressure baseline, control returns to block 704 where pressure and/or vibration measurements are collected. If the cavitation analyzer 314 determines that the manipulated pressure exceeds the pressure baseline, the cavitation analyzer 314 sets a pre-cavitation alarm (block 710). The pre-cavitation alarm is displayed for an operator at the display 318. The pre-cavitation alarm informs the operator that the pump 120 is operating in a pre-cavitation state. Informing the operator of the pre-cavitation state enables the operator to facilitate correction of the pump 120 (e.g., to aid the pump 120 in returning to a normal operation state) before significant damage is done to the pump 120.

The example process of FIG. 7 determines if the manipulated vibration exceeds a vibration baseline at the cavitation analyzer 314 (block 712). The vibration baseline is used in the comparison according to the baseline parameters set at block 702. For example, the cavitation analyzer 314 determines if the average vibration measurement exceeds a particular vibration baseline at a particular time (e.g., when the pre-cavitation alarm is set). If the cavitation analyzer 314 determines that the manipulated vibration does not exceed the vibration baseline, control returns to block 704 where pressure and/or vibration measurements are collected. If the cavitation analyzer 314 determines that the manipulated vibration exceeds the vibration baseline, the cavitation analyzer 314 sets a cavitation alarm (block 714). For example, the cavitation analyzer 314 may increase the pre-cavitation alarm to a higher warning level, may increase the pre-cavitation alarm to a cavitation alarm, and/or may create a new cavitation alarm. The cavitation alarm is displayed for the operator at the display 318. The cavitation alarm informs the operator that the pump 120 is operating at an increased pre-cavitation state or a cavitation state (e.g., the cavitation alarm is more urgent than the pre-cavitation alarm) to facilitate correction of the pump 120 (e.g., to aid the pump 120 in returning to a normal operation state) before significant damage is done to the pump 120. Control then returns to block 704 where pressure and/or vibration measurements are collected. In some examples, control returns to block 702 where the cavitation parameters are set or reset.

Figure 8:
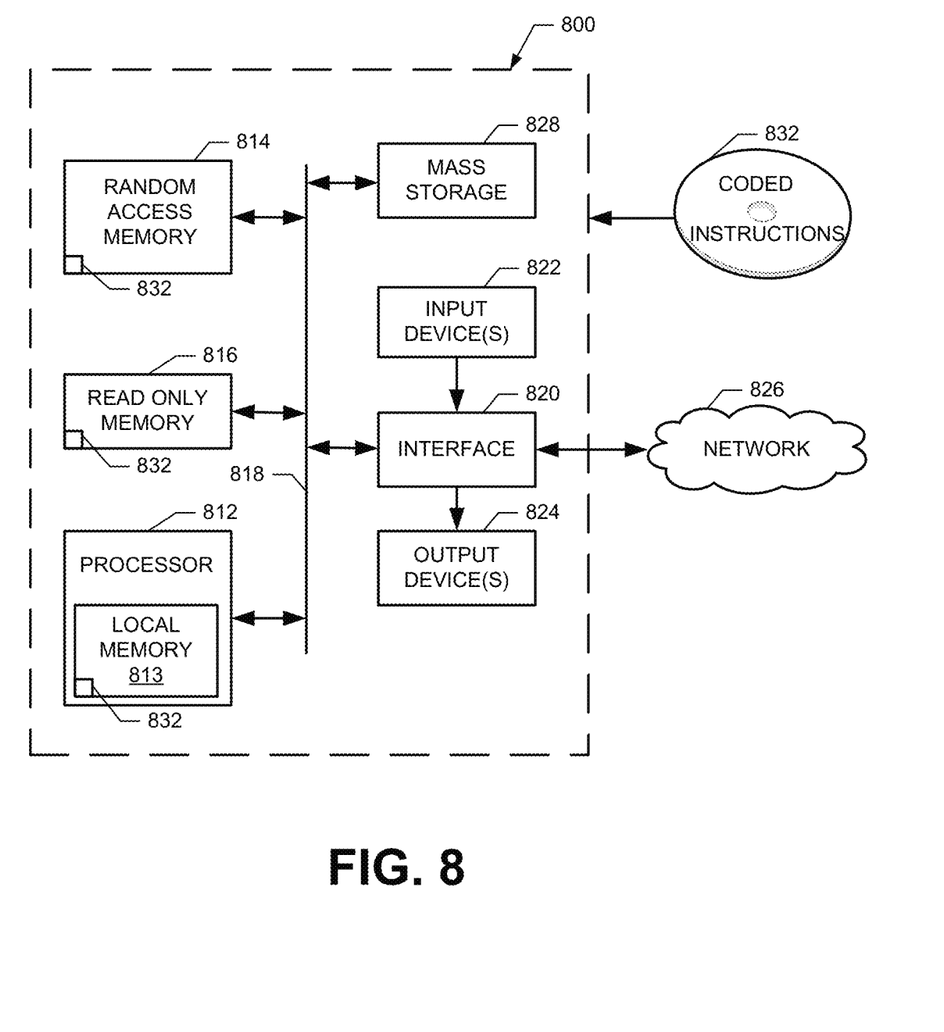
FIG. 8 is a schematic illustration of an example computer that may be used and/or programmed to carry out the example process of FIG. 7 and/or, more generally, to implement the example operator station 104 of FIGS. 1 and/or 3.

FIG. 8 is a schematic illustration of an example computer 800 that may be used and/or programmed to carry out the example process of FIG. 7 and/or, more generally, to implement the example application station 106 and/or operator station 104 of FIGS. 1 and/or 3. The computer 800 of the instant example includes a processor 812. For example, the processor 812 can be implemented by one or more microprocessors or controllers from any desired family or manufacturer.

The processor 812 includes a local memory 813 (e.g., a cache) and is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814 and 816 is controlled by a memory controller.

The computer 800 also includes an interface circuit 820. The interface circuit 820 may be implemented by any type of interface standard, such as an Ethernet interface, a universal serial bus (USB), and/or a PCI express interface. One or more input devices 822 are connected to the interface circuit 820. The input device(s) 822 permit a user to enter data and commands into the processor 812. The input device(s) can be implemented by, for example, a keyboard, a mouse, a touchscreen, a track-pad, a trackball, isopoint and/or a voice recognition system. One or more output devices 824 are also connected to the interface circuit 820. The output devices 824 can be implemented, for example, by display devices (e.g., a liquid crystal display, a cathode ray tube display (CRT), a printer and/or speakers). The interface circuit 820, thus, typically includes a graphics driver card.

The interface circuit 820 also includes a communication device such as a modem or network interface card to facilitate exchange of data with external computers via a network 826 (e.g., an Ethernet connection, a digital subscriber line (DSL), a telephone line, coaxial cable, a cellular telephone system, etc.).

The computer 800 also includes one or more mass storage devices 828 for storing software and data. Examples of such mass storage devices 828 include floppy disk drives, hard drive disks, compact disk drives and digital versatile disk (DVD) drives.

Coded instructions 832 to implement the example process of FIG. 7 may be stored in the mass storage device 828, in the volatile memory 814, in the non-volatile memory 816, and/or on a removable storage medium such as a CD or DVD.

Although certain example methods, apparatus and articles of manufacture have been described herein, the scope of coverage of this patent is not limited thereto. Such examples are intended to be non-limiting illustrative examples. On the contrary, this patent covers all methods, apparatus and articles of manufacture fairly falling within the scope of the appended claims either literally or under the doctrine of equivalents.

What is claimed is:

1. A method comprising:
    monitoring a pressure parameter and a vibration parameter associated with an asset in an operating process unit;
    calculating a manipulated pressure value based on the pressure parameter, wherein calculating the manipulated pressure value based on the pressure parameter includes calculating a standard deviation value of a set of pressure values;
    determining, based on the manipulated pressure value, a state of cavitation associated with the asset;
    in response to determining the state of cavitation is a pre-cavitation state, triggering an alarm;
    calculating a manipulated vibration value based on the vibration parameter; and
    changing a severity level of the alarm based on the manipulated vibration value.

2. The method of claim 1, wherein the state of cavitation associated with the asset is at least one of the pre-cavitation state or a cavitation state.

3. The method of claim 1, further comprising presenting the alarm in a display.

4. The method of claim 1, wherein calculating the manipulated pressure value based on the pressure parameter includes calculating an average standard deviation value for a plurality of calculated standard deviation values.

5. The method of claim 1, wherein determining the state of cavitation associated with the asset is the pre-cavitation state includes determining if the manipulated pressure value exceeds a baseline parameter by a first threshold.

6. The method of claim 5, wherein the baseline parameter corresponds to at least one of values of the pressure parameter measured when the asset is operating in a normal operating condition or a signature of values of the pressure parameter measured across an operating range of one or more corresponding variable state parameters.

7. The method of claim 5, wherein changing the severity level of the alarm includes:
    comparing the manipulated vibration value to a vibration baseline; and
    determining the asset is in a cavitation state if the manipulated vibration value exceeds the vibration baseline by a second threshold.

8. The method of claim 1, wherein calculating the manipulated vibration value based on the vibration parameter includes calculating a standard deviation value of a set of vibration values.

9. The method of claim 1, further comprising comparing the manipulated pressure value to a baseline parameter.

10. A system comprising:
    a monitoring application to monitor a pressure parameter and a vibration parameter associated with an asset in an operating process unit;
    a pressure analyzer to calculate a manipulated pressure value based on the pressure parameter, wherein, to calculate the manipulated pressure value based on the pressure parameter, the pressure analyzer is to:
        calculate a standard deviation value based on a plurality of pressure values; and
        calculate an average value of multiple standard deviation values;
    a cavitation analyzer to determine a state of cavitation associated with the asset based on the manipulated pressure value, the cavitation analyzer to, in response to determining the cavitation state is a pre-cavitation state, trigger an alarm indicative of the pre-cavitation state; and
    a vibration analyzer to calculate a manipulated vibration value based on the vibration parameter, wherein, based on the manipulated vibration value, the cavitation analyzer is to change the alarm to indicate a cavitation state.

11. The system of claim 10, wherein the alarm is to be presented to an operator.

12. The system of claim 10, wherein, to determine the state of cavitation associated with the asset, the cavitation analyzer is to:
    compare the manipulated pressure value to a pressure baseline; and
    determine the asset is in a pre-cavitation state if the manipulated pressure value exceeds the pressure baseline by a first threshold.

13. The system of claim 12, wherein the pressure baseline corresponds to at least one of the values of the pressure parameter measured when the asset is operating in a normal operating condition or a signature of values of the pressure parameter measured across an operating range of one or more corresponding variable state parameters.

14. The system of claim 12, wherein, to change the alarm, the cavitation analyzer is to:
    compare the manipulated vibration value to a vibration baseline; and
    determine the asset is in the cavitation state if the manipulated vibration value exceeds the vibration baseline by a second threshold.

15. A tangible computer readable storage medium comprising instructions that, when executed, cause a computing device to at least:
    monitor a pressure parameter and a vibration parameter associated with an asset in an operating process unit;
    calculate a manipulated pressure value based on the pressure parameter, wherein calculating the manipulated pressure value based on the pressure parameter includes calculating an average value of different standard deviation values corresponding to different sets of pressure values;
    determine, based on the manipulated pressure value, a state of cavitation associated with the asset;
    in response to the determined state of cavitation being a pre-cavitation state, trigger a pre-cavitation alarm;
    calculate a manipulated vibration value based on the vibration parameter; and
    change a severity level of the pre-cavitation alarm based on the manipulated vibration value.

16. The tangible computer readable medium of claim 15, wherein the state of cavitation associated with the asset is at least one of the pre-cavitation state or a cavitation state.

17. The tangible computer readable medium of claim 15, wherein the alarm is to be presented to an operator.

18. The tangible computer readable medium of claim 15, wherein determining the state of cavitation associated with the asset is the pre-cavitation state includes determining if the manipulated pressure value exceeds a baseline parameter by a first threshold.

19. The tangible computer readable medium of claim 18, wherein the baseline parameter corresponds to at least one of the values of the pressure parameter measured when the asset is operating in a normal operating condition or a signature of values of the pressure parameter measured across an operating range of one or more corresponding variable state parameters.

20. The tangible computer readable medium of claim 18, further comprising instructions that cause the computing device to:
  compare the manipulated vibration value to a vibration baseline; and
  determine the asset is in a cavitation state if the manipulated vibration value exceeds the vibration baseline by a second threshold.

* * * * *